(12) United States Patent
Bakshi

(10) Patent No.: US 7,732,648 B2
(45) Date of Patent: Jun. 8, 2010

(54) MULTISTAGE CATALYTIC PROCESS FOR OLEFIN ETHERIFICATION

(76) Inventor: Amarjit Singh Bakshi, Refining Hydrocarbon Technologies LLC, 20130 Chateau Bend Dr., Katy, TX (US) 77450

( * ) Notice: Subject to any disclaimer, the term of this patent is extended or adjusted under 35 U.S.C. 154(b) by 302 days.

(21) Appl. No.: 11/400,846

(22) Filed: Apr. 10, 2006

(65) Prior Publication Data

US 2007/0106098 A1 May 10, 2007

Related U.S. Application Data

(60) Provisional application No. 60/733,413, filed on Nov. 4, 2005.

(51) Int. Cl.
C07C 41/01 (2006.01)

(52) U.S. Cl. .................................. 568/697; 568/699
(58) Field of Classification Search ............... None
See application file for complete search history.

(56) References Cited

U.S. PATENT DOCUMENTS

| 5,621,150 | A | * | 4/1997 | Rastelli et al. | 568/697 |
| 5,908,964 | A | * | 6/1999 | Koskinen et al. | 568/697 |
| 5,919,989 | A | * | 7/1999 | Bakshi et al. | 568/698 |

FOREIGN PATENT DOCUMENTS

EP 0 590 632 A1 * 4/1994

* cited by examiner

*Primary Examiner*—Rosalynd Keys

(57) ABSTRACT

A process for producing ethers by reacting alcohols and olefins in successive catalytic stages is disclosed. The process includes alternating catalytic reaction stages and separation stages.

2 Claims, 7 Drawing Sheets

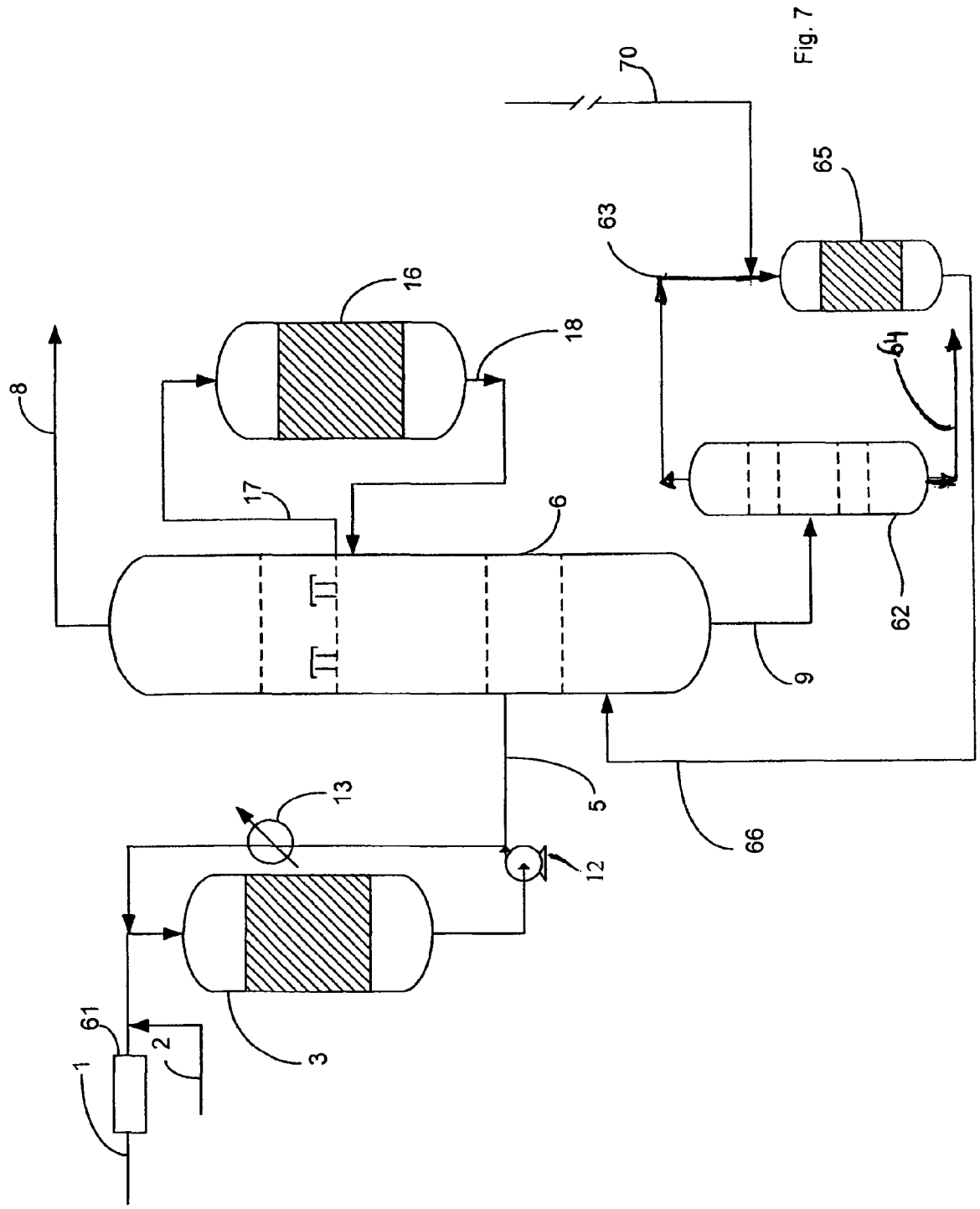

MULTISTAGE CATALYTIC PROCESS FOR OLEFIN ETHERIFICATION

Priority Earlier Filing: U.S. Pat. No. 60/733,413 dated Nov. 4, 2005.

FIELD OF THE INVENTION

The invention relates to producing ethers by reacting iso-olefins with alcohols in the presence of a catalyst. More specifically, the invention relates to a multistage reaction process and apparatus providing alternating reaction and separation stages.

BACKGROUND OF THE INVENTION

Low molecular weight unsymmetrical ethers such as methyl t-butyl ether (MTBE), t-amyl methyl ether (TAME), ethyl t-butyl ether (ETBE), t-amyl ethyl ether (TAEE), butyl t-butyl ether (BTBE), t-amyl butyl ether (TABE), isobutyl t-butyl ether (IBTBE), and t-amyl isobutyl ether (TAIBE) are commonly added to gasoline to increase the gasoline's octane number and lower the Reid vapor pressure (RVP) of the gasoline blend. Furthermore, the additional oxygen provided via the ethers contributes to better combustion and reduced CO in the combustion products. Also, adding ethers, which boosts the octane number of the gasoline, allows more harmful octane boosting components such as benzene and other aromatics to be scaled back in the mixture.

SUMMARY OF THE INVENTION

The present disclosure provides a process for producing ethers by reacting alcohol with iso-olefin in multiple reactors alternating with multiple separation phases. In general, alcohol and olefin are reacted in a first catalytic reaction stage. The effluent of the first reaction stage is provided to a column where the effluent is partially separated into light and heavy components, the heavy component containing ether. The light components are reacted in one or more additional catalytic reaction stages to increase the overall yield of ether. Between each of the additional reaction stages, the reaction mixtures are partially separated into light and heavy components, thus driving the equilibrium for ether production during each reaction stage.

The disclosed process has the advantage that it uses conventional ion exchange resin catalyst rather than specialized or proprietary catalyst. The process also has the advantage that catalyst beds can be changed without shutting down the process, thus allowing continual processing. Embodiments of the process are adapted to separate TBA from the product stream and thus can utilize wet alcohol feed. Expensive front-end alcohol drying can thus be avoided. These and other benefits will be apparent to one of skill in the art in view of the attached figures and discussion.

BRIEF DESCRIPTION OF THE DRAWINGS

FIG. 7 illustrates another process for utilizing wet alcohol, the process having a separation and reactor stage for separating and reacting a column bottom stream containing ether and TBA with additional alcohol to produce additional ether.

DETAILED DESCRIPTION OF THE INVENTION

Figure 1:
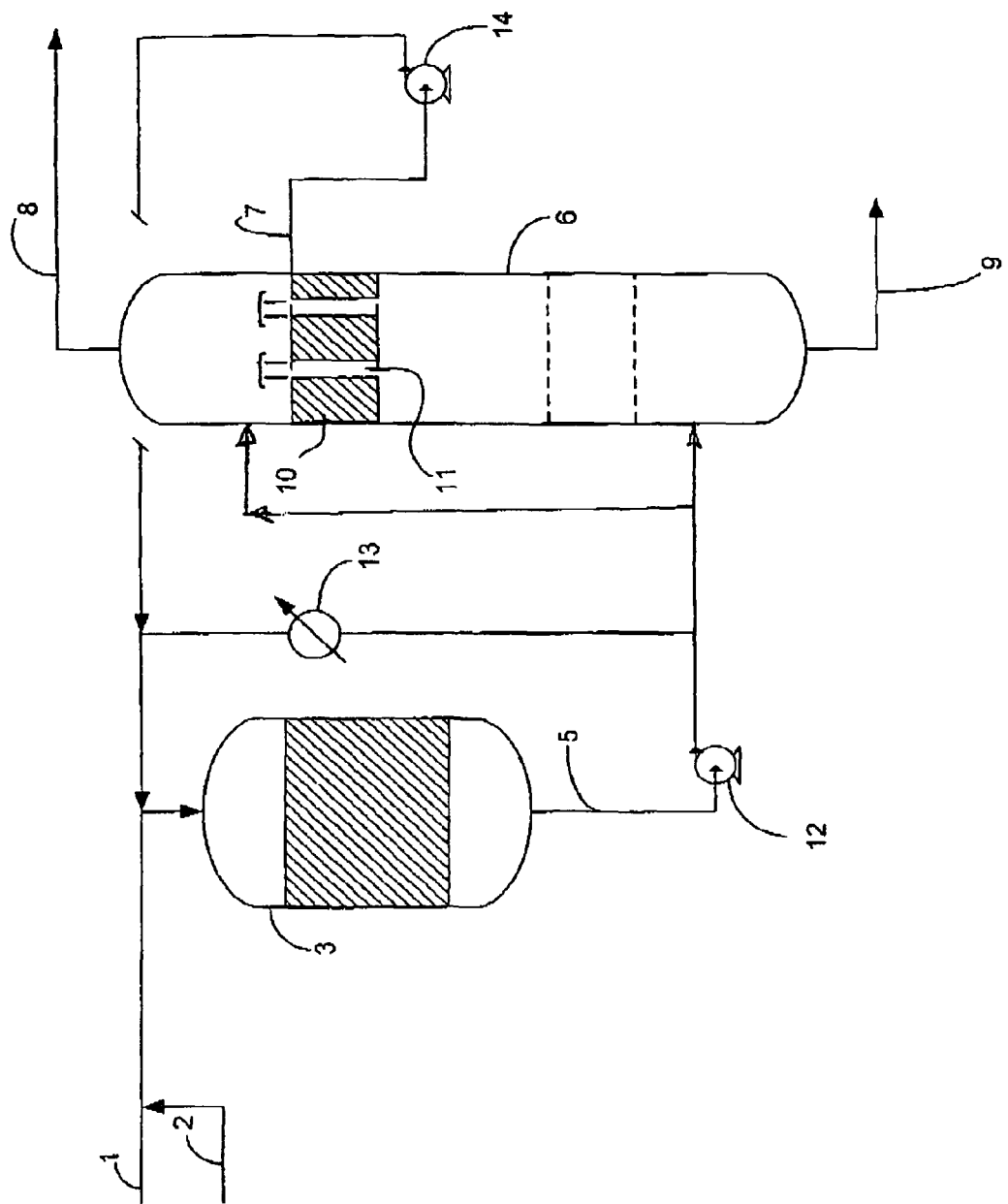
FIG. 1 is a simplified process flow diagram illustrating a process having a reaction stage contained within a column.

An aspect of the presently disclosure is a process for producing ethers from C4-C7 iso-olefins by reacting the olefin with alcohols, e.g., methanol, ethanol, propanol and isobutanol in the presence of an acid ion exchange resin catalyst. The etherification reactions take place in the liquid phase, because simultaneous reaction and separation, as practiced in the art, does not provide an advantage compared to alternate reaction and separation, as provided by the present disclosure. Furthermore, the presently disclosed method allows the use of bulk catalyst, stacked reactors/distillation, low cost catalyst installation without leakage, and convenient separation of reactants and products.

The disclosed methods and apparatuses can be understood by referring to the attached Figures, which are described in detail herein. It should be understood that pipelines are in fact being designated when streams are identified and that streams are intended, if not stated, when materials are mentioned. Moreover, flow control valves, temperature regulator devices, pumps, compressors, and the like are understood as installed and operating in conventional relationships to the major items of equipment which are shown in the drawings and discussed hereinafter with reference to the continuously operating process of this invention. All of these valves, devices, pumps, and compressors, as well as heat exchangers, accumulators, condensers and the like, are included in the term "auxiliary equipment". It is in the ability of one of ordinary skill in the art to implement such auxiliary equipment, as needed, in view of the present disclosure.

FIG. 1 illustrates an embodiment of the disclosed process. Iso-olefin feed 1 and alcohol feed 2 are provided to a stand alone reactor 3. Stand alone reactor 3 can be, for example a fixed bed reactor. Effluent 5 from stand alone reactor 3 is provided to column 6. Heavy components 9, including ether and DIB, go to the bottom of column 6 and lighter components such as alcohol, hydrocarbons and DME go overhead 8. The column can include a strainer to keep catalyst particles from the effluent. The lighter components go to the stacked reactors 10 in column 6. Stacked reactors 10 are catalyst bed reactors that operate in liquid phase reaction mode. The vapor bypasses the reactor via vapor chimneys 11 and condensate is exposed to the catalyst 10 as it returns down through reactors 10. A cut 7 can be returned as feed to stand alone reactor 3. Pumps 12 and 14 and chiller 13 illustrated in FIG. 1 is known to those of skill in the art, and such auxiliary equipment need not be discussed in detail.

In the embodiment illustrated in FIG. 1, reactants will be exposed to two reactor sections; stand alone reactor 3 and stacked reactor section 10 in column 6. As will be discussed in more detail below, additional reactor sections can be added, either as additional stacked reactors or as side reactors, to increase the yield of ether. Suitable catalysts used in the reactors include supported catalysts such as macroreticular polystyrene sulfonic acid resin catalysts. Specific examples of suitable catalysts include Amberlyst 15, Amberlyst 35, Dowex M31 and 32, and Purolite CT-175. It is within the ability of one of skill in the art to select from these and other catalysts depending on their particular design constraints. According to a preferred embodiment, catalyst beds can be changed while the system is in operation.

Figure 2:
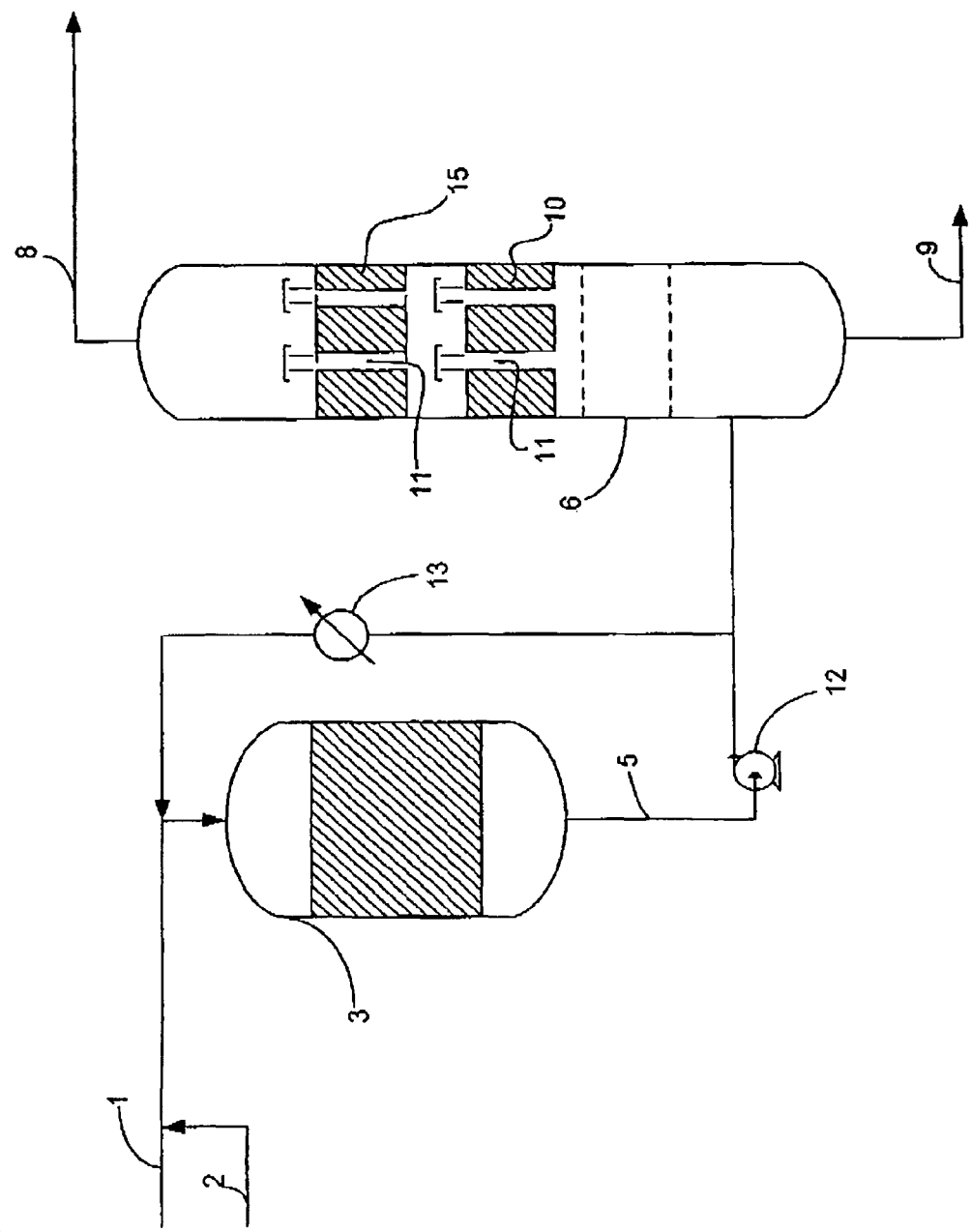
FIG. 2 illustrates a process having two reaction stages contained within a column.

FIG. 2 illustrates a process having an additional stacked reactor 15. Comparing the embodiments illustrated in FIGS. 1 and 2, the process of FIG. 1 having stand alone reactor 3 and one stacked reactor 10 might yield an iso-olefin conversion of about 97%, whereas the process of FIG. 2 might yield a conversion of about 99.8%, the increase being due to the additional reactor 15.

Figure 3:
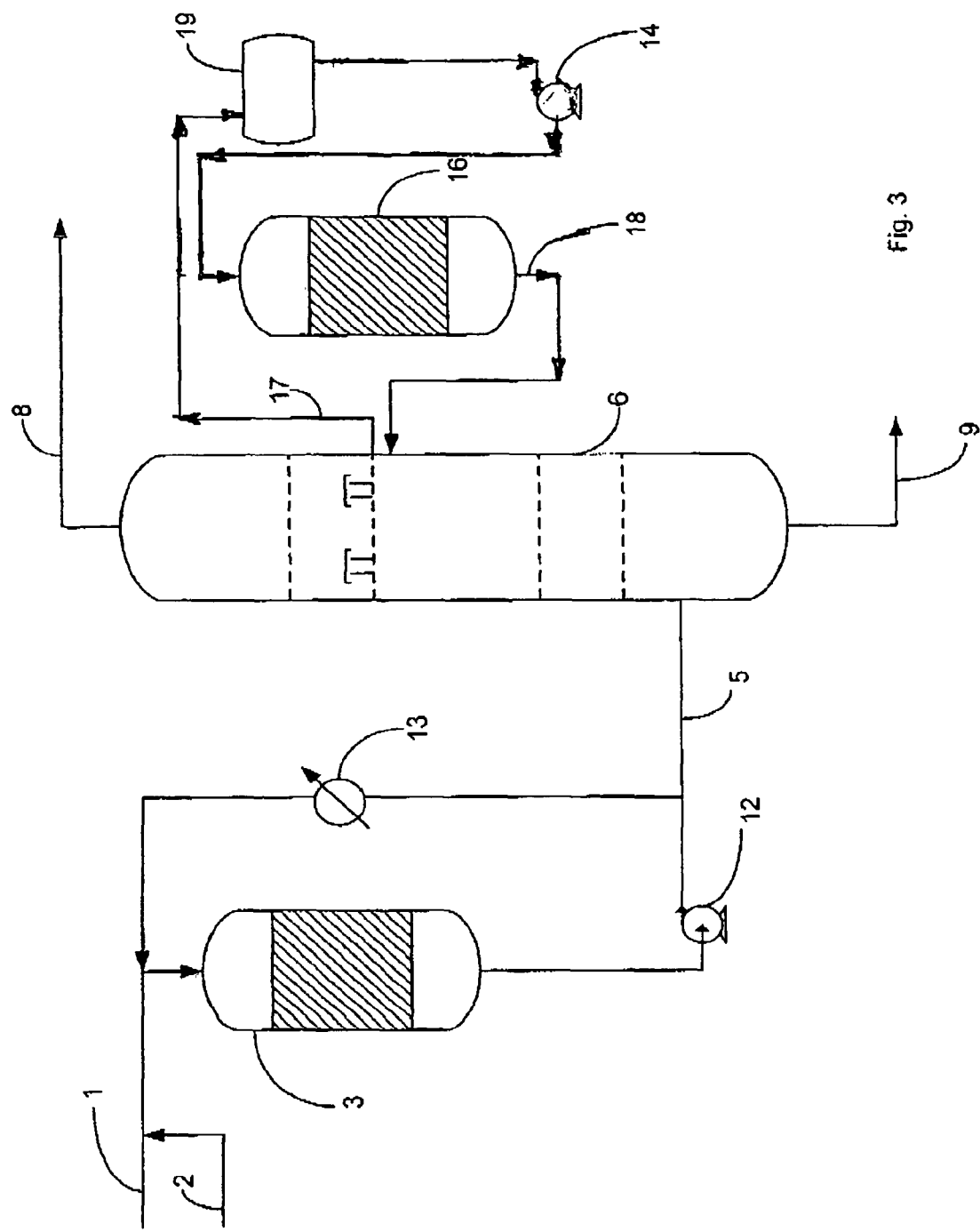
FIG. 3 illustrates a process having a side reactor stage.

FIG. 3 illustrates an embodiment having a side reactor 16, rather than stacked reactor. Side reactor can be, for example, a fixed bed reactor. A fraction of the lighter components 17 from column 6 are directed through side reactor 16. Effluent 18 from reactor 16 can be recycled through reactor 16 or returned to column 6. As stated above, pump 14 and vessel 19, as well as additional auxiliary equipment is known to those of skill in the art and need not be described in detail here.

Figure 4:
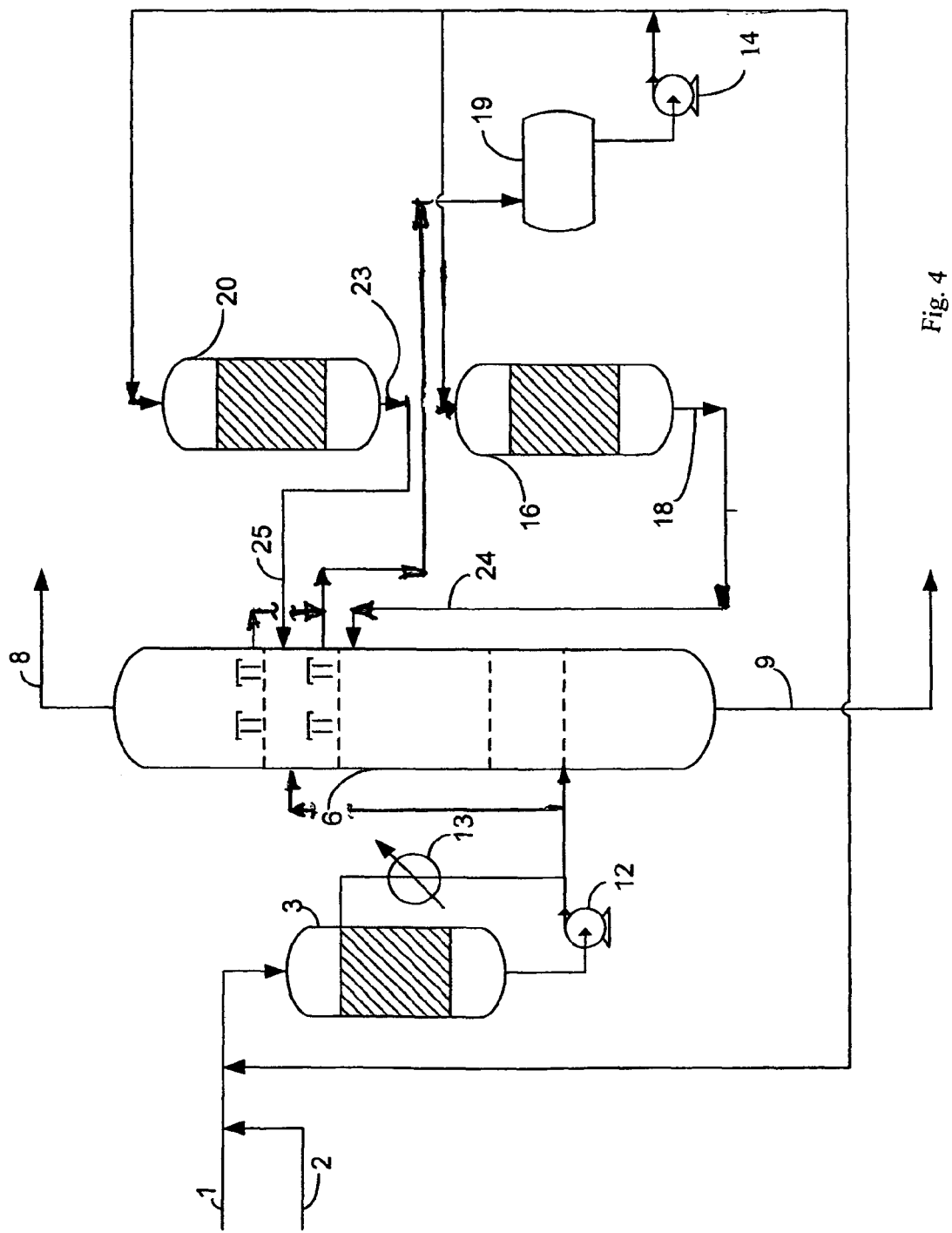
FIG. 4 illustrates a process having two side reactor stages.

FIG. 4 illustrates an embodiment having two side reactors, 16 and 20. A portion of effluent 18 and 23, from reactors 16 and 20, respectively, can be returned to column 6 via lines 24 and/or 25. A portion of effluent can also be combined in vessel 19 and returned to side reactors 18 and 20 and/or to stand alone reactor 3.

One of skill in the art will appreciate that disclosed herein is a process for producing ethers from C4-C7 iso-olefins and lower alcohols such as methanol and ethanol via reaction in a fixed bed reactor followed by a reaction system installed in a column or side reactor to a column. The reactors can utilize bulk macroporous polystyrene sulfonic acid resin catalyst. The process generally involves reacting the olefins feedstock and aliphatic alcohol in a fixed bed reactor upstream of a distillation column, close to equilibrium conditions forming tertiary alkyl ether. The reactor effluent is sent to a distillation column where unreacted hydrocarbons and alcohols are partly separated by trays or packing and reactants go up and ether product and heavier hydrocarbons go down. Iso-olefins from the hydrocarbon feed and alcohol are reacted in a second stage of the reaction system to produce ether at an iso-olefins conversion above equilibrium levels. The second stage reaction section can be part of the distillation column with bulk catalyst installed above the feed location. The heavier reaction products, e.g., ether, go down from the second stage of reaction and unreacted iso-olefin, C4, hydrocarbon and alcohol goes up through the trays. A third stage reaction section can be installed, providing greater iso-olefin conversion, for example, for isobutylene and methanol. The third stage can provide greater than 99 percent conversion. The third reaction stage can be located above the second stage in the column and there can be separation trays located between the second and third stages.

Alternatively, the second and third stage reactors can be side reactors to the column rather than integrated with the column. The processes described herein provides alternating reaction and separation stages. More reaction stages can be installed, if desired, for example up to about 15 reaction stages.

Examples of suitable alcohols include methanol, ethanol, butanol, isopropanol, and isobutanol. Most typically methanol or ethanol is used. Olefins can be pure or mixed. Typically mixed olefins contain iso-olefins of C4-C7 and most typically contain isobutylene and/or iso-amylenes. Olefinic feed stock typically contains about 7 to about 60% tertiary olefin.

The first stage of the reaction typically operates at about 50 to about 70 degrees C. and provides close to equilibrium conversion. For example, for iso-butylene, conversion is typically about 90% and for iso-amylene the conversion is typically about 65%. The second and third stage reactors typically operate at about 60 to about 70 degrees C. and provide conversion above the equilibrium limit. Conversion for isobutylene is typically greater than about 97 to about 99% and iso-amylene about 90%. Ether products include MTBE, ETBE, TAME, and TAEE.

Figure 5:
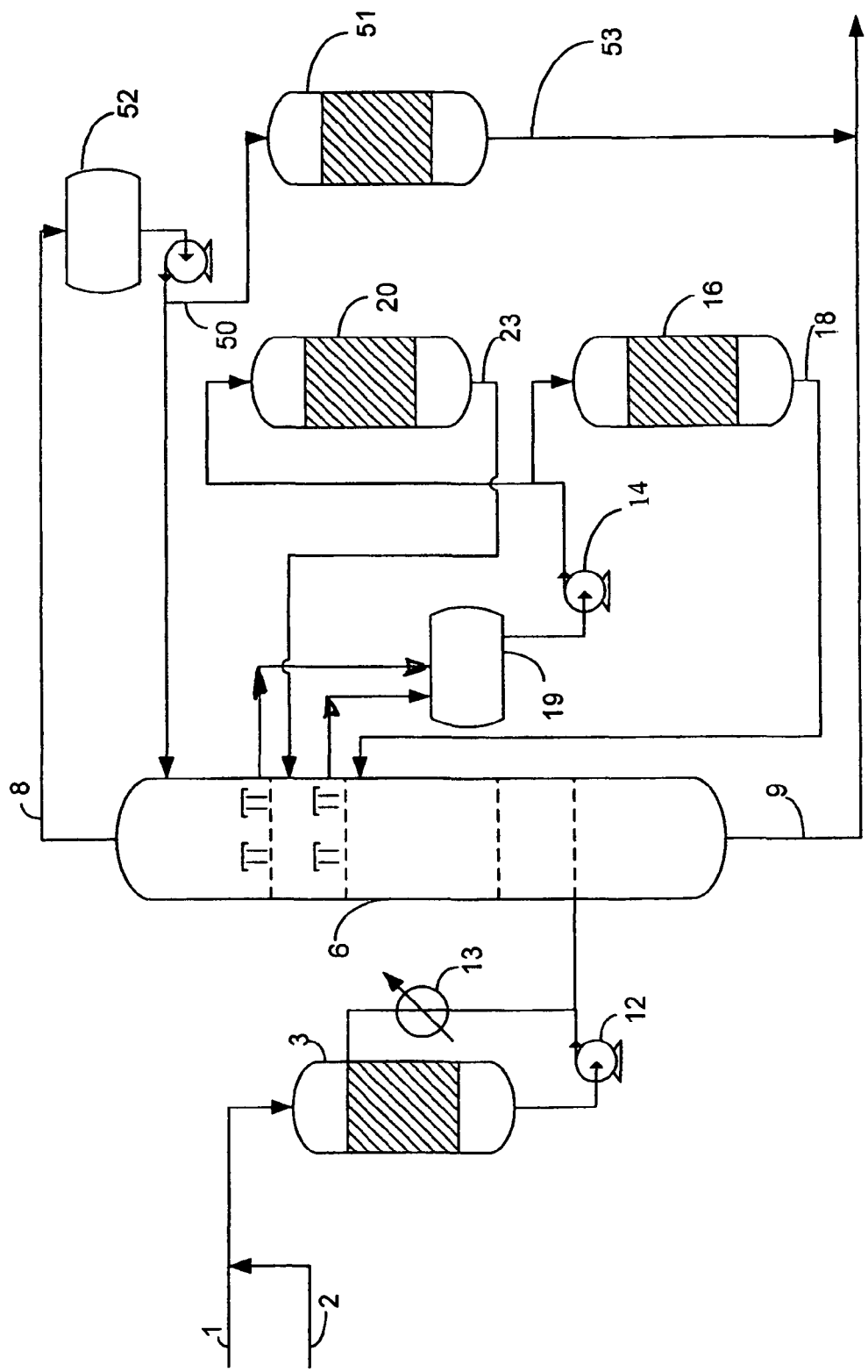
FIG. 5 illustrates a process having two side reactor stages and an additional reactor stage for reacting a column top stream.

FIG. 5 illustrates an embodiment particularly suited for prossessing C5+ hydrocarbons. Light reactants 8 exiting as the overhead of column 6 are collected in vessel 52. A portion of the collected reactants are routed to an additional reactor 51 via a slipstream 50. Reactor effluent 53 is combined with column effluent 9 to provide a mixture of ether and C5+, which can be blended with gasoline.

Figure 6:
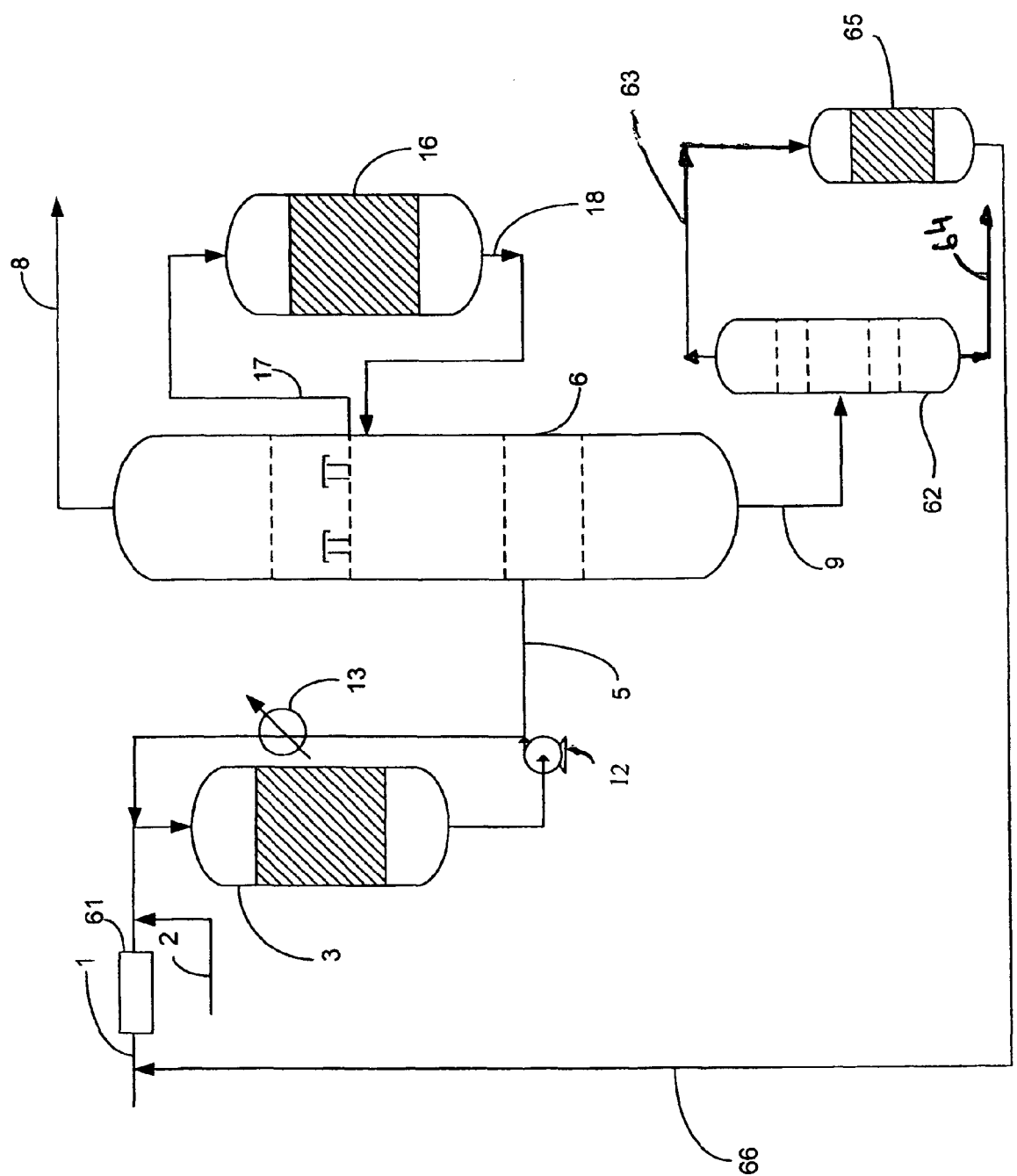
FIG. 6 illustrates a process for utilizing wet alcohol, the process having a separation and reactor stage for separating and reacting a column bottom stream containing ether and TBA.

FIG. 6 illustrates an embodiment particularly suited for processing wet alcohol, for example wet ethanol. The process can include a water wash 61 in the iso-olefin feed 1. According to one embodiment, column effluent 9 might contain higher than desirable amount of tert-butyl alcohol (TBA). In such a case, effluent 9 can be delivered to column 62. Ether product, for example ETBE, leaves column 62 as an overhead stream 63 and effluent 64 containing TBA enters a catalytic stage 65. Catalytic stage 65 can include resin catalyst and/or a zeolite catalyst for converting the TBA to iso-olefin and water. Effluent 66 from catalytic stage 65 is returned to iso-olefin feed 1.

FIG. 7 illustrates an alternative embodiment suited for processing wet alcohol. The process can include a water wash 61 in the iso-olefin feed 1. According to one embodiment, column effluent 9 might contain higher than desirable amount of tert-butyl alcohol (TBA). In such a case, effluent 9 can be delivered to column 62. Ether product, for example ETBE, leaves column 62 as an overhead stream 63 and effluent 64 containing TBA enters a catalytic stage 65. Catalytic stage 65 can include resin catalyst and/or a zeolite catalyst. Additional alcohol, e.g., ethanol is provided to catalytic stage 65 via stream 70 to force the equilibrium toward producing ether product. Effluent 66 from catalytic stage 65 is returned to column 6.

EXAMPLES

The following examples for illustrate MTBE and TAME production using feeds having the composition:

| C4 feed (wt %) | | C4 feed (wt %) | |
| --- | --- | --- | --- |
| C3 | 1.0 | C4 | 0.6 |
| Isobutane | 31.7 | 3-methyl-1-butene | 1.4 |
| n-butene | 9.8 | Isopentane | 37.4 |
| Butene-1 | 14.5 | 1-pentene | 6.5 |
| Isobutylene | 15.3 | 2-methyl-1-butene | 8.6 |
| Butadiene | 0.6 | n-pentane | 5.8 |
| Trans-2-butene | 15.0 | Trans-2-pentene | 12.8 |
| Cis-2-butene | 11.6 | Cis-2-pentene | 7.7 |
| C5+ | 0.5 | 2-methyl-2-butene | 16.0 |
| | | Pentadienes | 1.2 |
| | | C6+ | 2.0 |
| | 100 | | 100 |

The following reaction conditions and yields are provided:

| | MTBE | TAME |
| --- | --- | --- |
| Stand alone reactor | | |
| Inlet temp. (F.) | 100-140 (120) | 120-150 (140) |
| Pressure (psig) | 120-150 (110) | 70-90 (65) |
| LHSV (Hr$^{-1}$) | 3-8 (4) | 1-2 (2) |
| Iso-olefin conversion (%) | 90-92 (90) | 65-70 (68) |
| Distillation Column Reactor | | |
| Inlet temp. (F.) | 140-160 (145) | 155-170 (160) |
| Pressure (psig) | 90-120 (110) | 55-75 (65) |
| LHSV (Hr$^{-1}$) | 3-8 (4) | 1-3 (2) |
| Iso-olefin conversion (%) | 80-98 (90) | 60-90 (80) |

The disclosed process is further discussed in the attached appendix.

What is claimed is:

1. A process for producing ethers, comprising:

reacting iso-olefin with wet alcohol in a first catalytic reaction stage to provide a first reaction mixture; the first reaction mixture is sent to a first evaporation column for separating the first reaction mixture to provide a first light component fraction and a first heavy component fraction comprising ether; withdrawing a portion of the first light component fraction and reacting it in a second catalytic reaction stage to provide a second reaction mixture, which is recycled back to the first evaporation column; in the first evaporation column separating the second reaction mixture to provide a second light component fraction and a second heavy component fraction comprising ether; the first and second light component fractions exit the top of the column as a first overhead stream and the first and second heavy component fractions exit the bottom of the column as a first bottoms stream comprising ether and TBA; the first bottoms stream comprising ether and TBA is sent to a second evaporation column for separating the first bottoms stream to provide a second overhead stream comprising ether and a second bottoms stream comprising TBA; reacting the second bottoms stream comprising TBA in a catalytic reactor to generate an effluent comprising iso-olefin, which is recycled to the first catalytic reaction stage.

2. A process for producing ethers, comprising:

reacting iso-olefin with wet alcohol in a first catalytic reaction stage to provide a first reaction mixture; the first reaction mixture is sent to a first evaporation column separating the first reaction mixture to provide a first light component fraction and a first heavy component fraction comprising ether; withdrawing a portion of the first light component fraction and reacting in a second catalytic reaction stage to provide a second reaction mixture, which is recycled back to the first evaporation column; in the first evaporation column separating in the second reaction mixture to provide a second light component fraction and a second heavy component fraction comprising ether, the first and second light component fractions exit the top of the column as a first overhead stream and the first and second heavy component fractions exit the bottom of the column as a first bottoms stream comprising ether and TBA; the first bottoms stream comprising ether and TBA is sent to a second evaporation column for separating the first bottoms stream to provide a second overhead stream comprising ether and a second bottoms stream comprising TBA; reacting the second bottoms stream with alcohol in a catalytic reactor to generate an effluent comprising ether; and recycling the effluent to the first evaporation column.

* * * * *